(12) United States Patent
Boone et al.

(10) Patent No.: US 8,596,130 B2
(45) Date of Patent: Dec. 3, 2013

(54) INSPECTION VEHICLE FOR A TURBINE DISK

(71) Applicant: Westinghouse Electric Company LLC, Cranberry Township, PA (US)

(72) Inventors: Paul J. Boone, Bethel Park, PA (US); Jeffrey Monaco, McDonald, PA (US); Tom Nenno, Murrysville, PA (US); Richard Fredenberg, Harrison City, PA (US); Corey Adamonis, Latrobe, PA (US); Benjamin Bachman, Athens, TN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 0 days.

(21) Appl. No.: 13/671,666

(22) Filed: Nov. 8, 2012

(65) Prior Publication Data

US 2013/0061664 A1    Mar. 14, 2013

Related U.S. Application Data

(63) Continuation of application No. 12/826,789, filed on Jun. 30, 2010, now Pat. No. 8,333,116.

(51) Int. Cl.
*G01M 13/00* (2006.01)

(52) U.S. Cl.
USPC ............................ 73/660; 73/112.01; 73/593

(58) Field of Classification Search
USPC .................. 73/660, 584, 593, 661, 112.1; 324/207.25
See application file for complete search history.

(56) References Cited

U.S. PATENT DOCUMENTS

| | | | |
|---|---|---|---|
| 4,310,796 A * | 1/1982 | Braithwaite et al. | 324/220 |
| 4,811,091 A | 3/1989 | Morrison et al. | |
| 4,995,320 A | 2/1991 | Sato et al. | |
| 5,164,826 A | 11/1992 | Dailey | |
| 5,263,107 A | 11/1993 | Ueda et al. | |
| 5,781,007 A | 7/1998 | Partika et al. | |
| 5,942,690 A | 8/1999 | Shvetsky | |
| 6,707,297 B2 | 3/2004 | Nath et al. | |
| 6,972,561 B2 | 12/2005 | Fields et al. | |
| 7,019,537 B2 | 3/2006 | Hazel et al. | |
| 7,075,296 B2 | 7/2006 | Moore | |
| 7,950,297 B2 | 5/2011 | Moore et al. | |
| 8,207,730 B2 * | 6/2012 | Martin et al. | 324/209 |
| 8,333,116 B2 * | 12/2012 | Boone et al. | 73/660 |
| 2002/0088282 A1 | 7/2002 | Zayicek et al. | |
| 2002/0190682 A1 | 12/2002 | Schempf et al. | |
| 2004/0091076 A1 | 5/2004 | Kerr et al. | |
| 2009/0229365 A1 | 9/2009 | Bentzel | |
| 2012/0060611 A1 | 3/2012 | Thommen-Stamenkov et al. | |

* cited by examiner

*Primary Examiner* — J M Saint Surin
(74) *Attorney, Agent, or Firm* — Richard J. Coldren; Westinghouse Electric Company LLC (57) ABSTRACT

An inspection vehicle structured to inspect a portion of the turbine disk, preferably the blade attachment hubs, while the turbine disk is disposed within a turbine housing assembly is provided. A turbine disk is generally planar but includes an inner hub and an outer blade attachment hub. The inner hub is coupled to a shaft and the blade attachment hub provides a surface to which removable blades are attached. The area between the inner hub and outer blade attachment hub is substantially planar. The inner and blade attachment hubs are the "inspection areas" that the inspection vehicle is structured to inspect. The inspection vehicle travels over, and is magnetically coupled to the planar surface between the two hubs.

20 Claims, 8 Drawing Sheets

FIG. 9

INSPECTION VEHICLE FOR A TURBINE DISK

CROSS REFERENCE TO RELATED APPLICATIONS

This application is a continuation application of application Ser. No. 12/826,789, filed Jun. 30, 2010, entitled INSPECTION VEHICLE FOR A TURBINE DISK.

BACKGROUND OF THE INVENTION

1. Field of the Invention

The present invention relates to a device for inspecting a turbine disk and, more specifically, to a device for inspecting a turbine disk in situ.

2. Related Art

Turbine disks used as pan of a power generation system must be inspected for cracking and other defects as a part of normal maintenance. Typically, such inspections are performed by ultrasonic transducers, eddy current probes, and similar devices. Traditionally, the inspection of turbine, disks require the disk assembly to be removed from the turbine housing assembly. This is a time consuming, labor intensive, and expensive process. One improvement over this system provided for an ultrasonic transducer, or other inspection device, to be mounted on an elongated arm having a tip structured to fit between turbine disk assemblies. This inspection system does not allow for the turbine, disk assembly to remain in the turbine, housing assembly. To provide access to the turbine disks, the turbine disks had to be removed from the turbine housing assembly. The turbine disk assembly is then placed on, and rotated under, a generally stationary inspection device.

SUMMARY OF THE INVENTION

The disclosed and claimed concept provides for an inspection vehicle structured to inspect a portion, of the turbine disk, preferably the blade attachment hubs, while the turbine disk is disposed within a turbine housing assembly. A turbine disk is generally planar but includes a inner huh and an outer blade attachment hub. The inner hub is coupled to a shaft and the blade attachment hub provides a surface to which removable blades are attached. The area between the inner hub and outer blade attachment hub is substantially planar. The inner and blade attachment hubs are the "inspection areas" that the inspection vehicle is structured to inspect The inspection vehicle travels over, and is magnetically coupled to, a planar surface between the two hubs.

The inspection vehicle is substantially autonomous; being able to move over the surface of the turbine disk with little, or no, input from a user. The inspection vehicle includes an elongated body structured to support a plurality of components, a magnetic coupling assembly coupled to the vehicle body and structured to movably couple the vehicle body to the turbine disk, a drive assembly structured to move the vehicle body over the turbine disk, and an inspection assembly structured to inspect the turbine disk hubs.

The magnetic coupling assembly is used to couple the inspection vehicle to the turbine disks in situ, i.e. in an operational position, wherein the plane of the disks extends generally vertically. The drive assembly includes a plurality of wheels, preferably four, wherein each wheel both steers and is linked to a drive motor. The drive assembly further includes a sensor and a control unit. The sensors, including ultrasonic transducers structured to detect the inner diameter location of the inner disk hub, encoders on the wheels structured to track distance traveled, and a gravitational sensor, to provide data enabling the inspection vehicle to track its circumferential location in the turbine disk. The drive assembly is further structured to drive the inspection vehicle over the surface of the turbine disk with either little or no user interaction. The inspection assembly is structured to support an ultrasonic transducer for inspecting either of the turbine disk hubs, in this configuration, a single user may operate the inspection vehicle.

BRIEF DESCRIPTION OF THE DRAWINGS

A further understanding of the invention can be gained, from the following description of the preferred embodiments when read in conjunction with accompanying drawings in which.

DESCRIPTION OF THE PREFERRED EMBODIMENT

As used herein, a turbine disk "in situ" means that the turbine disk is in its operating position within a turbine housing.

As used herein, "operatively engage" and when used in connection with a gear, gear-like device, or an axle means that two or more elements contact each other in such a manner that rotation of one element causes the other element to rotate as well.

As used herein, a magnet "operatively spaced" from another element capable of magnetic attraction means that the two elements are so close as to allow the magnet to be attracted to the other element with a sufficient force so that, if the magnet is not restrained, the magnet would move into contact with the other element.

As used herein, "coupled" means a link between two or more elements, whether direct or indirect, so long as a link occurs.

As used herein, "directly coupled" means that two elements are directly in contact with each other.

As used herein, "fixedly coupled" or "fixed" means that two components are coupled so as to move as one while maintaining a constant orientation relative to each other. For example, a wheel with a "fixed axle" means that the wheel and the axle move as one component. Thus, a rotational force applied to the axle causes the wheel to rotate.

Directional designations, e.g., upper, lower, above, vertical, horizontal, are generally related to the views shown in the associated figures and are not limiting upon the claims.

Figure 1:
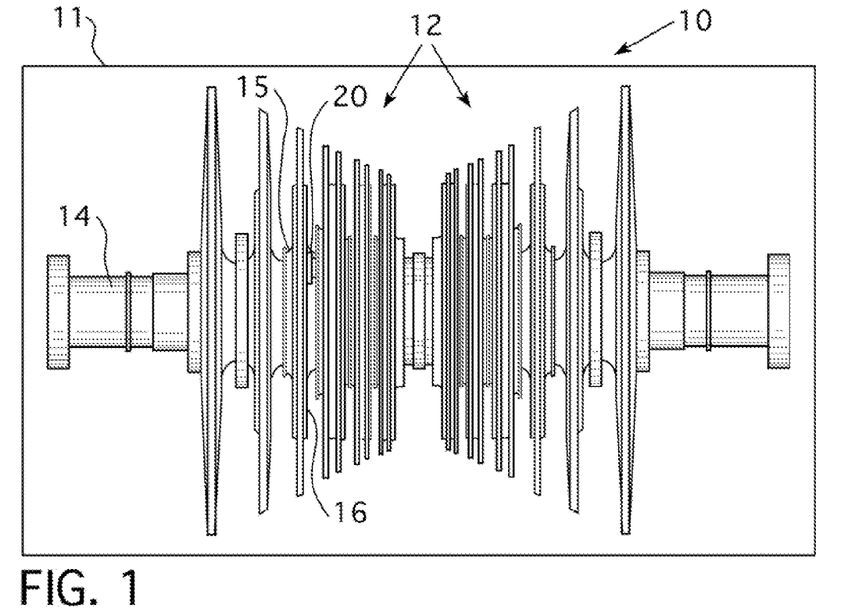
FIG. 1 is a schematic view of a turbine assembly.
Figure 2:
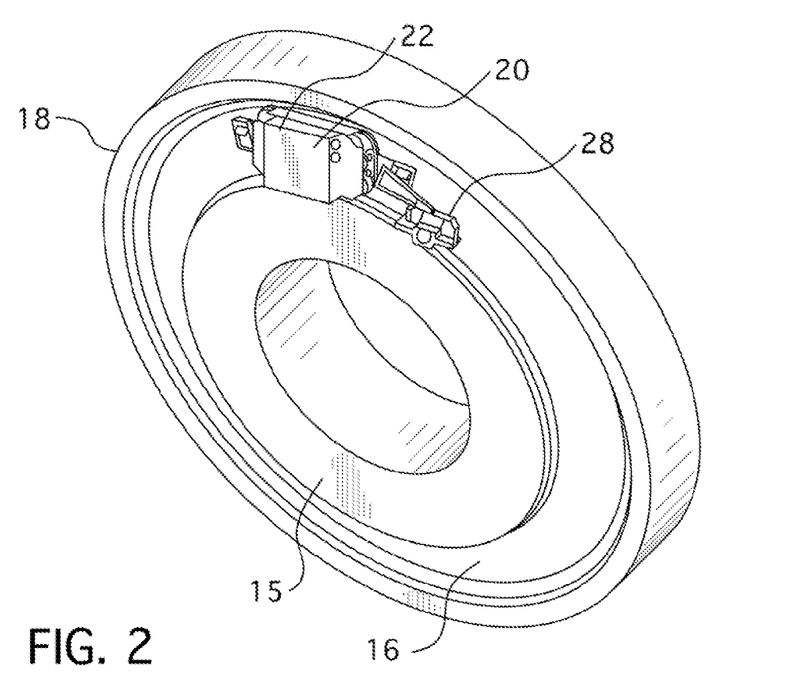
FIG. 2 is an isometric view of a turbine disk and inspection vehicle.

As shown schematically in FIG. 1, a turbine assembly 10 includes a housing 11 (shown schematically) a plurality of disks 12 coupled to a shaft 14. The shaft 14 of the turbine assembly 10 extends generally horizontally. Thus, the planar surfaces 16 of the turbine disks 12 extend generally radially. Each turbine disk 12 includes a inner hub 15, a radial planar surface 16 on each side of the turbine disk 12 and a outer hub 18 (not shown in FIG. 1, shown in FIG. 2). The radial planar surface 16 provides the surface over which an inspection vehicle 20 is structured to travel, as shown in FIG. 2.

Figure 3:
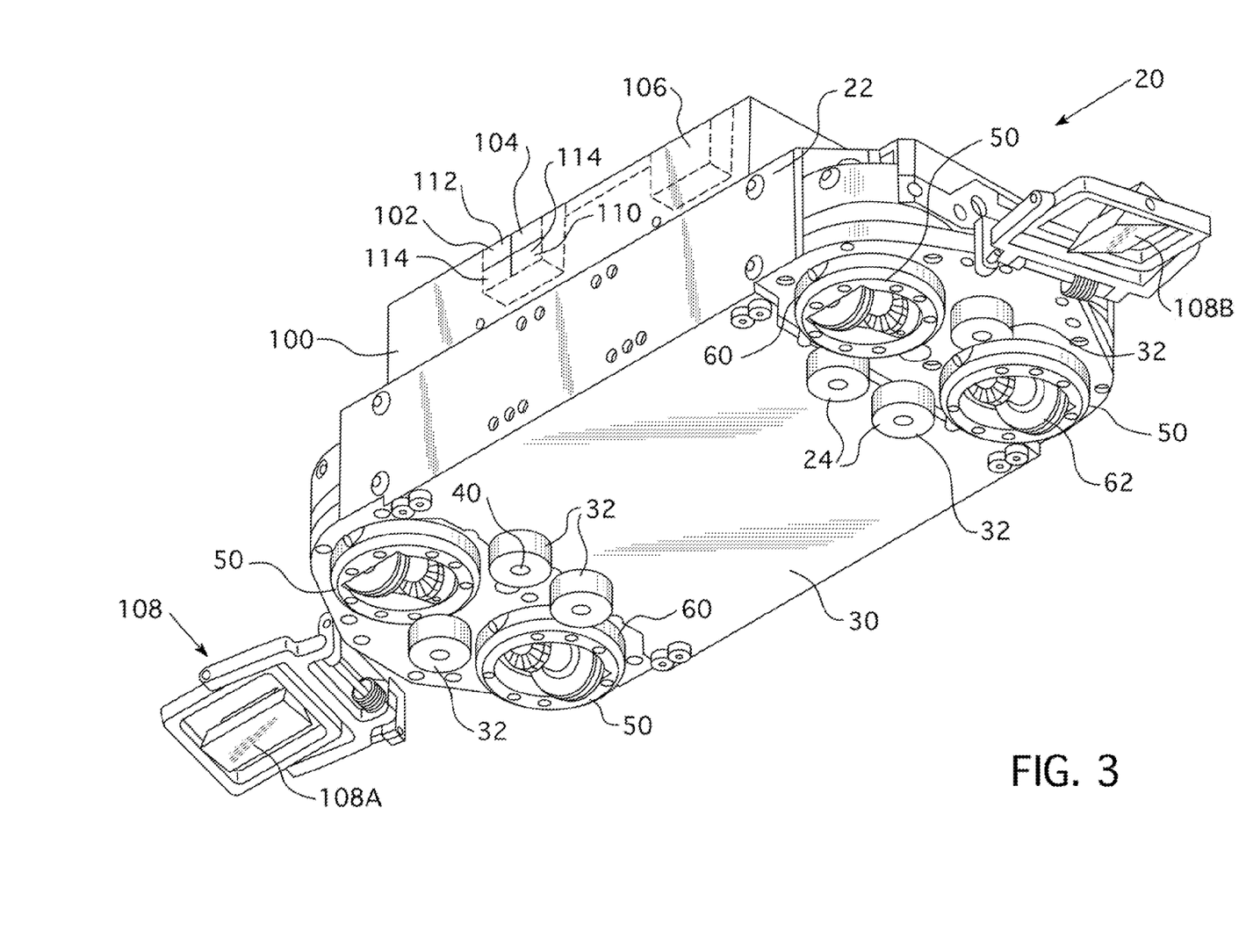
FIG. 3 an isometric view of an inspection vehicle without an inspection assembly.
Figure 4:
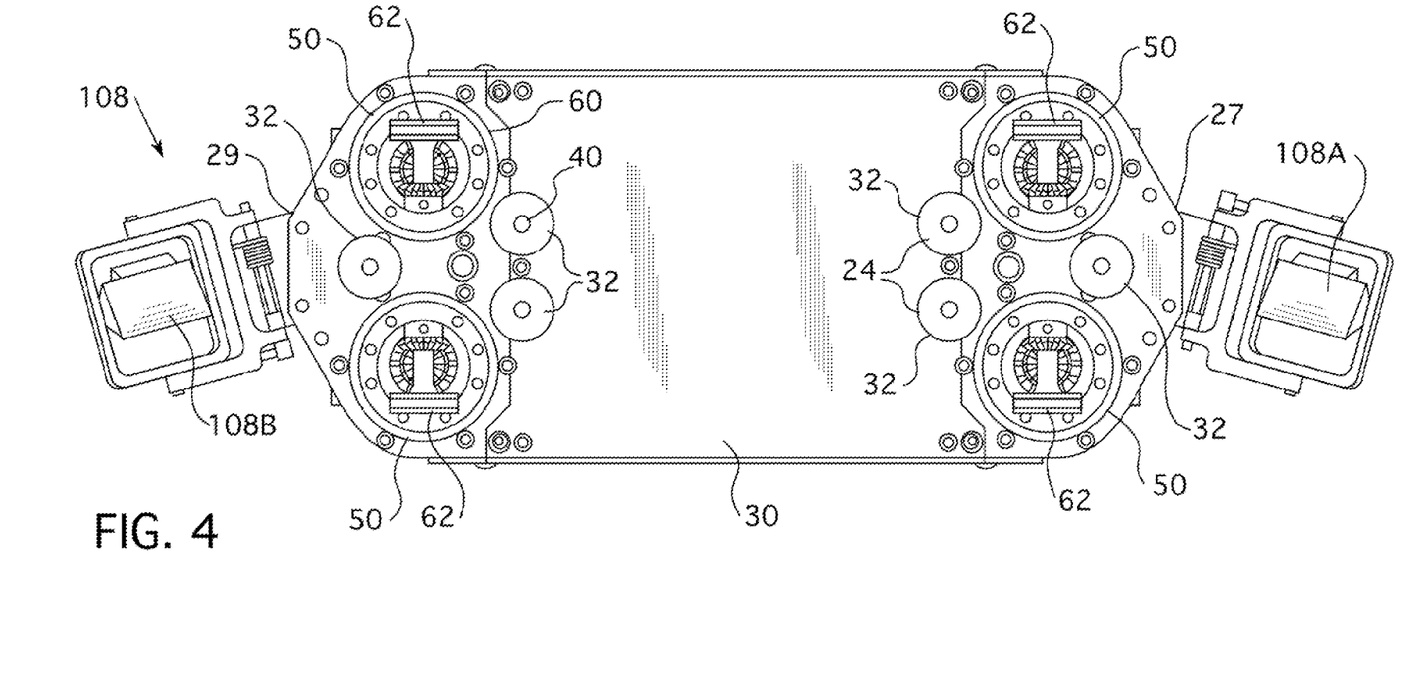
FIG. 4 is a bottom view of a inspection vehicle without an inspection assembly.
Figure 5:
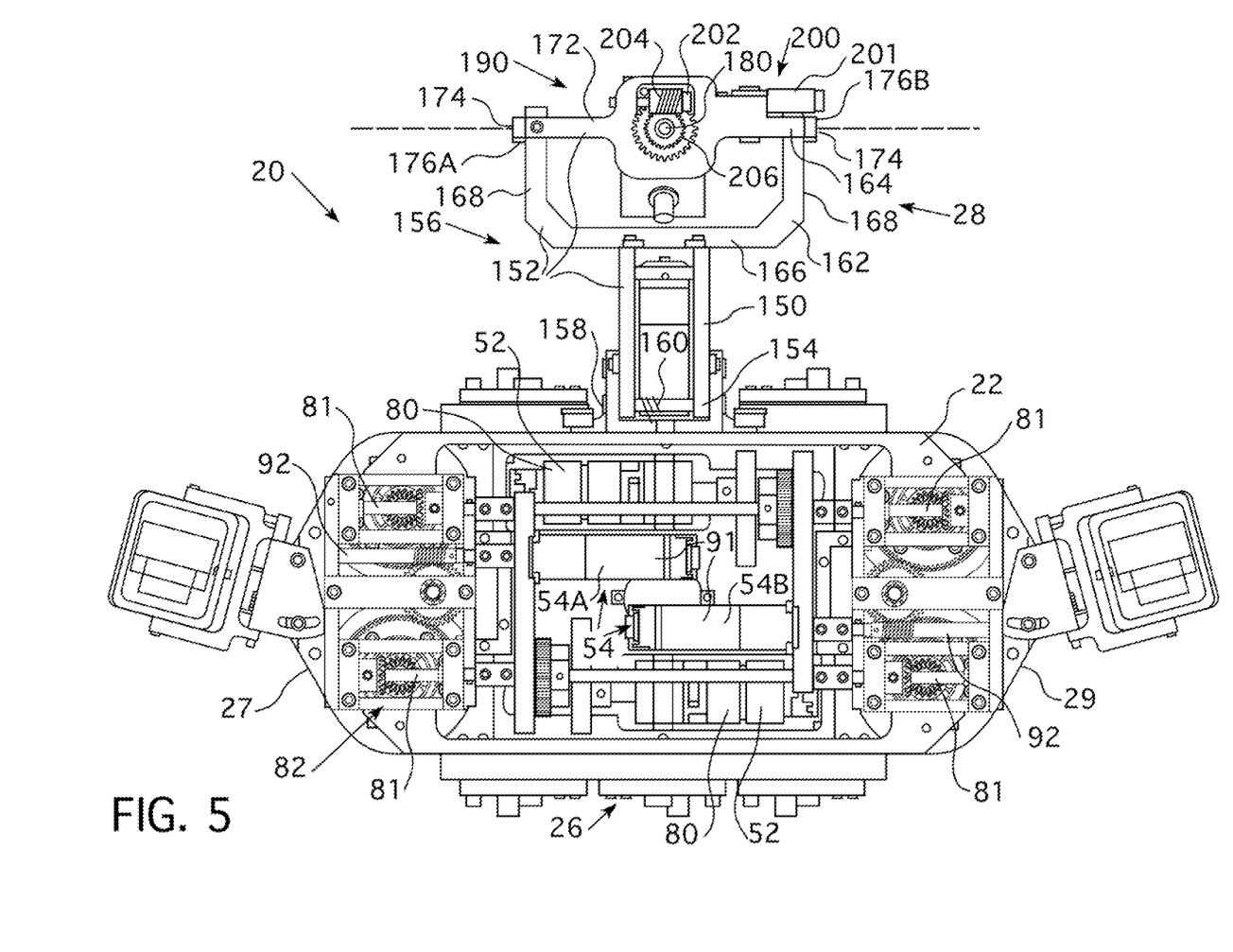
FIG. 5 is an top view of an inspection vehicle with an inspection assembly.

As shown in FIG. 1-5, the inspection vehicle 20 includes a body 22, a magnetic coupling assembly 24 (FIGS. 3 and 4), a motion assembly 26 (FIG. 5), and an inspection assembly 28 (FIG. 5). As shown in FIG. 3-5, generally, the vehicle body 22 is structured to support a plurality of components such as, but not limited to, the magnetic coupling assembly 24 (FIGS. 3 and 4), the motion assembly 26 (FIG. 5), and the inspection assembly 28 (FIG. 5). The vehicle body 22 is, preferably, elongated having a leading edge 27 and a trailing edge 29. Generally, the vehicle body 22 moves toward the leading edge 27, however, the vehicle body 22 may move in reverse toward the trailing edge 29, or if the wheel assembly wheels 62 (discussed below) are oriented generally sideways to the longitudinal axis of the vehicle body 22, the vehicle body 22 may move sideways.

Generally the magnetic coupling assembly 24 is coupled to the vehicle body 22 and structured to movably couple the vehicle body 22 to the turbine disk 12 that is being inspected. It is understood that, unless otherwise noted, the "turbine disk" hereinafter refers to the turbine disk 12 that is being inspected. Also, the motion assembly 26 is structured to move the vehicle body 22 over the turbine disk 12 and the inspection assembly 28 is structured to inspect the turbine disk inner hub 15 and blade attachment hub 18.

As noted above, the radial planar surface 16 (FIG. 2), extends generally vertically when the turbine disk 12 is in situ. Thus, the inspection vehicle 20 must be structured to travel over such a vertical surface. This is accomplished by the magnetic coupling assembly 24. The vehicle body 22 has a wheel side 30, which is the side adjacent to the planar surface 16. As used herein, directional terms and phrases related to the vehicle body 22 shall be independent of the vehicle body's 22 physical orientation/direction. Instead, directional terms and phrases related to the vehicle body 22 shall be phrased as if the vehicle body 22 is like an automobile traveling over a horizontal surface. Thus, for example, the vehicle body 22 "top" or "upper" side is that side which is furthest from the turbine disk 12. Accordingly, as the magnetic coupling assembly 24 is disposed on the vehicle body wheel side 30, the magnetic coupling assembly 24 is disposed adjacent to the planar surface 16. The magnetic coupling assembly 24 includes a plurality of magnets 32 coupled to body wheel side 30. As shown, there are six magnets 32 in the magnetic coupling assembly 24. There may be any number of magnets 32, however, depending upon the weight of the vehicle body 22 and the strength of the magnets 32. The magnets 32 are operatively spaced from the turbine disk 12. It is noted that the turbine disk 12 includes ferrous metals to which magnets are attracted. Further, the amplitude, i.e. strength, of the magnetic attachment force may be controlled by adjusting the spacing between the magnets 32 and the turbine disk 12. Thus, at least one magnet in the plurality of magnets 32 is coupled to the vehicle body 22 by an adjustable coupling device 40, such as, but not limited to an adjustment screw, whereby the spacing between the turbine disk 12 and the at least one magnet 32 coupled to the body 22 by an adjustable coupling device 40 may be altered.

As shown in FIG. 5, the motion assembly 26 includes a plurality of wheel assemblies 50, a plurality of wheel drive assemblies 52, and a plurality of turning assemblies 54. Each wheel assembly 50 is a substantially contained unit having elements structured to rotate the wheel assembly 50 relative to the vehicle body 22 (i.e. turn the wheel), and elements structured to rotate the wheel 62 about the wheel's axis (i.e. drive the wheel). That is, elements of both the wheel drive assemblies 52 and the turning assemblies 54 are incorporated into, or disposed within, each wheel assembly 50.

Figure 6:
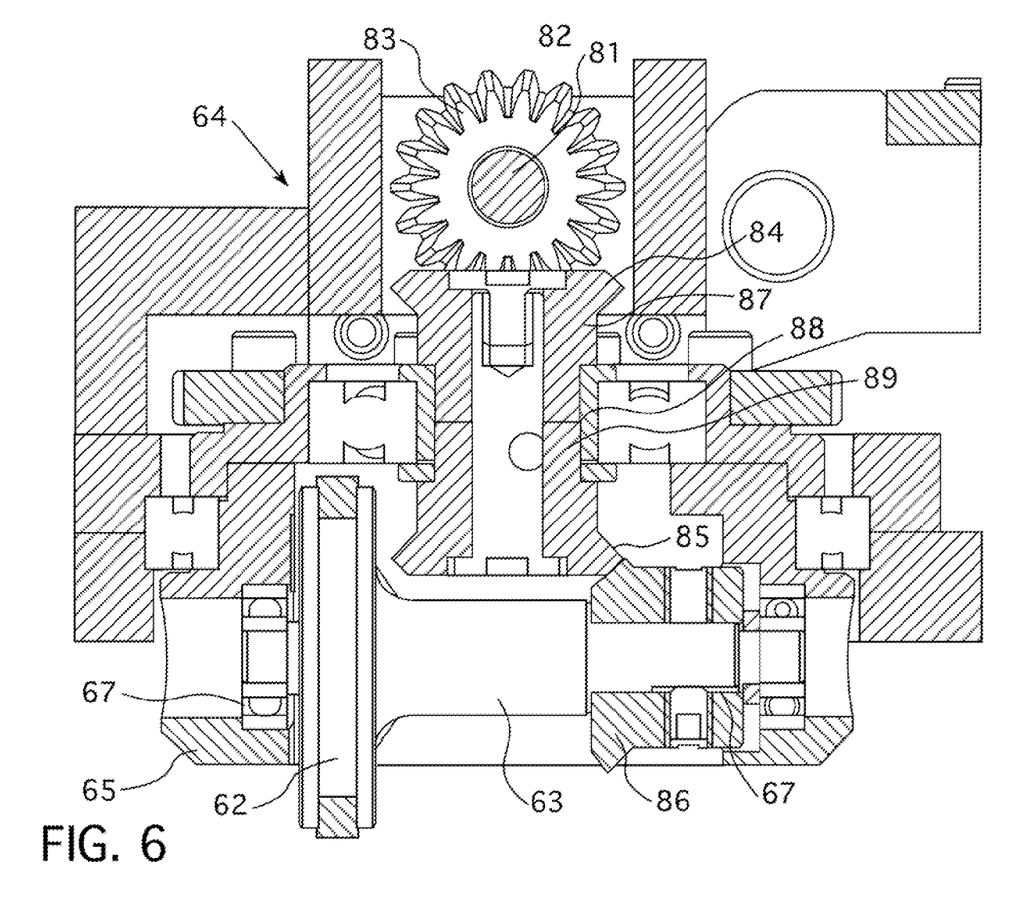
FIG. 6 is a detail cross-sectional view of a wheel assembly and bevel gear assembly.
Figure 7:
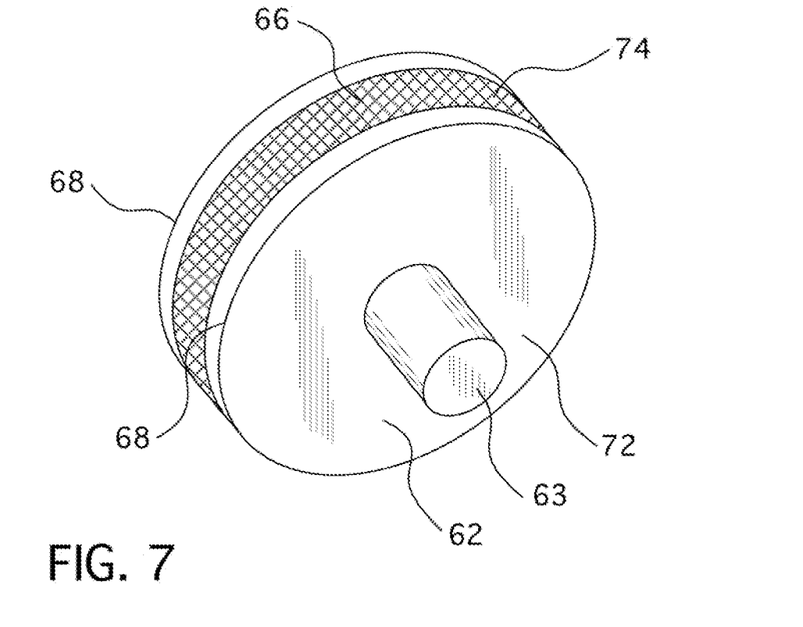
FIG. 7 is an isometric view of a wheel.

There are at least three, and preferably four, wheel assemblies 50. The wheel assemblies 50 are, in the preferred embodiment, disposed in a generally rectangular pattern. Each wheel assembly 50 includes a generally circular housing, assembly 60 and a wheel 62 having a fixed axle 63 (FIG. 7). That is, the axle 63 is fixed to the wheel assembly wheel 62 and rotates therewith. Each wheel assembly housing assembly 60 is generally cylindrical. As shown in FIG. 6, each wheel assembly housing assembly 60 comprises a plurality of stacked toroid members 64. The specific nature of each toroid member 64 is not relevant to this invention other than to note that the toroid members 64 are structured to support the elements of the wheel drive assemblies 52 and the turning assemblies 54. For example, one toroid member 64 is a bushing structured to extend about the second bevel gear 84 to protect the second bevel gear 84 from contacting other elements of the wheel assembly housing assembly 60. It is noted, however, that the lowest (closest to the turbine disk 12) toroid member 65 includes a pair of openings 67 disposed on opposite sides of the toroid member axis. The wheel axle 61 is disposed within the openings 67. Thus, the axis of each wheel assembly wheel 62 is in a fixed orientation relative to the associated wheel assembly housing assembly 60.

Each wheel assembly housing assembly 60 is oriented so that, when the vehicle body 22 is coupled to the turbine disk 12, each wheel assembly housing assembly 60 axis, and the axis for the toroid members 64, extends generally perpendicular to the surface of the turbine disk 12. Each wheel assembly housing assembly is rotatably coupled to the vehicle body 22. Thus, in this configuration each wheel assembly housing 60 is structured to rotate relative to the vehicle body 22. Further, as the orientation of each wheel axis is fixed relative to the wheel assembly housing, assembly 60, rotation of the wheel assembly housing, assembly 60 causes the associated wheel assembly wheel 62 to turn relative to the vehicle body 22.

As shown in FIG. 5 and as discussed below, the inspection assembly 28 (FIGS. 5 and 6) and the position control assembly 104 include ultrasonic transducers 108A, 108B. As such transducers are highly sensitive with regard to positioning, the wheels 62, shown in FIG. 7, must be structured to have a substantially constant radius. That is, the each wheel 62 must be rigid. At the same time, however, the wheels 62 must provide sufficient traction for the inspection vehicle 20 to travel over generally vertical surfaces. Thus, each wheel assembly wheel 62 includes an outer surface 66 having a rigid portion 68, extending about the circumference of the outer surface 56, and a pliable portion 70, extending about the circumference of the outer surface 66. The rigid portion 68 is, preferably, steel. The pliable portion 70 is, preferably rubber. More specifically, each wheel 62 preferably has a steel body 72 defining a circumferential groove (not visible). A rubber insert 74 is disposed within the groove. The rubber insert 74 is structured to have a thickness substantially corresponding to the depth of the groove. In this configuration, the outer circumferential steel portion of the wheel body 72 defining the groove and the outer surface of the insert 74 have the substantially the same radius and both define the wheel outer surface 66. In operation, the steel portion of the wheel outer surface 66 maintains the spacing; of the vehicle body 22 from the turbine disk 12 and the rubber portion of the wheel outer surface 66 provides traction. Finally, it is noted that the axis of each wheel 62 extends generally perpendicular to the axis of the wheel assembly housing 60. That is when assembled, the axis of each wheel 62 extends generally parallel to the planar surface 16.

As shown in FIG. 5, the inspection vehicle 20 includes at least one, and preferably two wheel drive assemblies 5.2; there may, however, be more wheel drive assemblies 52. In the preferred embodiment, there are two wheel drive assemblies 52 wherein each wheel drive assembly 52 provides power to two of the four wheel assemblies 50. Each wheel drive assembly 52 includes a motor 80 having an elongated output shaft 81 and a bevel gear assembly 82 for each wheel assembly 50. Each wheel drive assembly motor output shaft 81 extends across two wheel assemblies 50. In the preferred embodiment, each wheel drive motor assembly 52 is disposed between a wheel assembly 50 adjacent the leading edge 27 and a wheel assembly 50 adjacent the trailing edge 29. In this configuration, the wheel drive assembly motor output shaft 81 extends generally parallel to the longitudinal axis of the vehicle body 22. When the wheel drive assembly 52 is disposed between the wheel assembly 50 adjacent the leading edge 27 and a wheel assembly 50 adjacent the trailing edge 29, the wheel drive assembly motor output shaft 81 extends from two opposing sides of the wheel drive motor 80.

It is understood that the bevel gear assembly 82 for each wheel assembly 50 is substantially similar and that each bevel gear assembly 82 is coupled to, and powered by, a wheel drive assembly motor output shaft 81. Accordingly, the following discussion will address a single bevel gear assembly 82 but it is understood that each wheel assembly 50 has an associated bevel gear assembly 82. As shown in FIG. 6, each bevel gear assembly 82 includes a first bevel gear 83, a second bevel gear 84, a third bevel gear 85, and a fourth bevel gear 86. The second and third bevel gears $4, 85 each have a toroid collar 87, 89 extending from the back side of the associated bevel gear 84, 85 and about the axis of the associated bevel gear 84, 85. The distal ends of the toroid collars 87, 89 are coupled and the second and third bevel gears 84, 85 are maintained in a fixed orientation to each other. Thus, the second and third bevel gears 84, 85 form a bevel gear shaft 88 wherein the second and third bevel gears 84, 85 are disposed at the distal ends of the bevel gear shaft 88. Preferably, each bevel gear is angled about forty-five degrees.

A wheel drive assembly motor output shaft 81 extends over each wheel assembly 50 at a location substantially near the axis of the wheel assembly 50. The first bevel gear 83 is fixed to the wheel drive assembly motor output shaft 81 and is positioned to engage the bevel gear shaft 88. The bevel gear shall 88 longitudinal axis extends substantially along the wheel assembly housing assembly 60 axis. That is, the bevel gear shaft 88 extends, substantially, through the center of the wheel assembly housing assembly toroid members 64. Preferably, at least one wheel assembly housing assembly toroid member 64, such as, but not limited to a bushing, has an inner diameter structured to contact and support the bevel gear shaft 88. That is, the at least one wheel assembly housing assembly toroid member 64, such as, but not limited to a bushing, is structured to position the bevel gear shaft 88 substantially centrally within the wheel assembly 50. The fourth bevel gear 86 is fixed to the wheel axle 63.

The first bevel gear 83 engages the second bevel gear 84. The third bevel gear 85 engages the fourth bevel gear 86. In this configuration, each bevel gear assembly 82 is structured to convert the motion of the wheel drive assembly motor output shaft 81 from a horizontal rotation to a vertical rotation, and back to a horizontal rotation. Accordingly, the wheel drive assembly 52 is structured to cause an associated wheel assembly wheel 62 to rotate. That is, when the wheel drive assembly motor 80 is actuated the wheel drive assembly motor output shall Si rotates. Rotation of the wheel drive assembly motor output shaft 81 causes the first bevel gear 83 to rotate. As the first bevel gear 83 engages the second bevel gear 84, the second bevel gear 84 rotates as well. As the second and third bevel gears 84, 85 are in a fixed orientation on the bevel gear shaft 88, rotation of the second bevel gear 84 causes the third bevel gear 85 to rotate. As the third bevel gear 85 engages the fourth bevel gear 86, rotation of the third bevel gear 85 causes the fourth bevel gear 86 to rotate. As the fourth bevel gear 86 is fixed to the wheel assembly wheel axel 63, rotation of the fourth bevel gear 86 causes the wheel assembly wheel axel 63 to rotate. As the wheel assembly wheel axel 63 is fixed to the wheel assembly wheel 62, rotation of the wheel assembly wheel axel 63 causes the wheel assembly wheel 62 to rotate. Thus, the bevel gear assembly 82 operatively engages both the wheel drive assembly motor output shaft 81 and an associated wheel 62.

Figure 8:
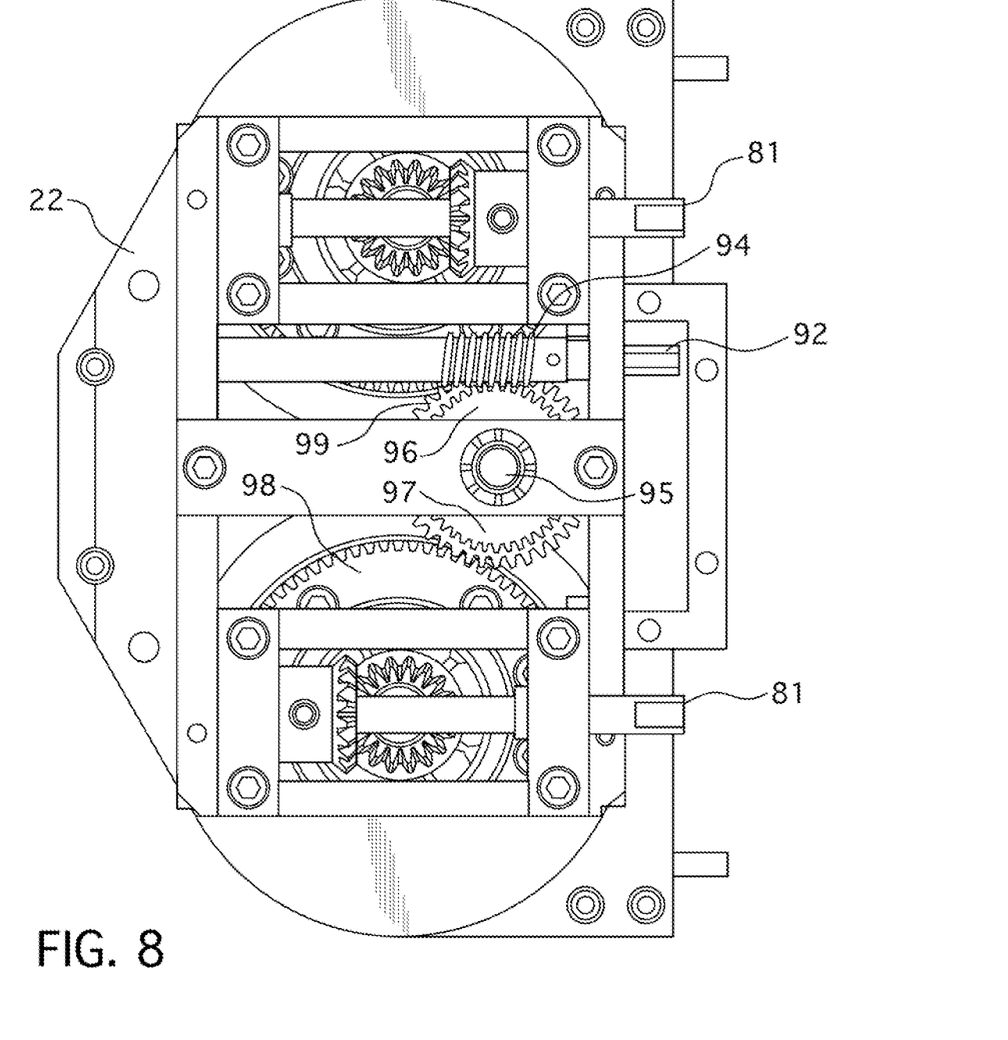
FIG. 8 is a detail top view of a turning assembly.

Rotation of the wheel assemblies 50 relative to the vehicle body 22, i.e. turning, is accomplished by the turning assemblies 54 (FIG. 5). As with the wheel drive assemblies 52, there are preferably, two turning assemblies 54 for the four wheel assemblies 50. In the preferred embodiment, there is a turning assembly 54A that is structured to turn the two wheel assemblies 50 adjacent the leading edge 27 and another turning assembly 54B that is structured to turn the two wheel assemblies 50 adjacent the trailing edge 29. In this configuration, the two wheel assemblies 50 adjacent the leading edge 27 turn at the same time and the two wheel assemblies 50 adjacent the trailing edge 29 turn at the same time As shown in FIG. 8, each turning assembly 54A, 54B includes a motor 91 (FIG. 5) having an output shaft 92, a worm gear 94, a central gear assembly 96, and an outer gear 98. The central gear assembly 96 includes a first gear 97 and a second gear 99. The central gear assembly first and second gears 97, 99 are each fixed to a central gear assembly axle 95. As such, the central gear assembly first and second gears 97, 99 rotate together. The turning assembly central gear assembly first gear 97 is structured to engage the worm gear 94. The turning assembly central gear assembly second gear 99 is structured to engage the turning assembly outer gear 98. When there are two adjacent wheel assemblies 50, as in the preferred embodiment, the turning assembly central gear assembly second gear 99 is structured to simultaneously engage both turning assembly outer gears 98 on adjacent wheel assemblies 50. The outer gear 98 is fixed to the wheel assembly housing assembly 60. That is, the outer gear 98, or more specifically the teeth of the outer gear 98, extend about the outer surface of the wheel assembly housing assembly 60. As such. The outer gear 98 may be one of the toroid members 64 that forms the wheel assembly housing, assembly 60. Alternatively, the outer gear 98 may be fixed to the wheel assembly housing assembly 60.

As with the wheel drive assemblies 52, the turning, assemblies 54 are substantially similar and only one will be described hereinafter. It is understood that the two turning assemblies 54 have substantially similar components and operate in a substantially similar manner. The turning assembly motor 91 is coupled to the inspection vehicle body 22 with the turning assembly motor output shaft 92 extending generally parallel to the longitudinal axis of the inspection vehicle body 22. The turning assembly motor output shaft 92 extends at least to a location adjacent the turning assembly central gear assembly 96. The worm gear 94 is fixed to the turning assembly motor output shaft 92 adjacent to the turning assembly central first gear 97. Further, the worm gear 94 engages the turning assembly central gear first gear 97.

The turning assembly central gear assembly 96 is rotatably coupled to the vehicle body 22 with an axis extending generally perpendicular to the longitudinal axis of the inspection vehicle body 22 and, when the inspection vehicle is in use, extending in a plane generally parallel to the planar surface 16. The turning assembly central second gear 99 is disposed, generally, an equal distance between the wheel assemblies 50 adjacent the leading edge 27 or wheel assemblies 50 adjacent the trailing edge 29. Further, the turning assembly central second gear 99 operatively engages the outer gear 98 that is fixed to the wheel assembly housing assembly 60. If there are two adjacent wheel assemblies 50, then the turning assembly central second gear 99 engages the outer gear 98 on both of the adjacent wheel assemblies 50. In this configuration, rotation of the central gear 96 will cause the two adjacent wheel assembly housing assemblies 60 to move, i.e. rotate in relation to the vehicle body 22. In tandem. Moreover, when the wheel assembly housing assemblies 60 have generally the same diameter, which they preferably do, the rate of rotation of the wheel assembly housing assemblies 60 is substantially similar.

When assembled, the actuation of the turning assembly motor 91 causes the turning assembly motor output shaft 92 to rotate. Rotation of the turning assembly motor output shaft 92 causes the worm gear 94 fixed thereto to rotate. Rotation of the worm gear 94 causes the central gear assembly first gear 97 to rotate. As noted above, the central gear assembly first and second gears 97, 99 rotate together. Rotation of the central gear assembly second gear 99 causes at least one, and in the preferred embodiment two, outer gears 98 on the adjacent wheel assemblies 50 to rotate. As the outer gears 98 are fixed to the wheel assembly housing, assemblies 60, and as the wheel assembly housing assemblies 60 are rotatably couple to the vehicle body 22, rotation of the outer gears 98 cause the wheel assembly housing assemblies 60 to rotate relative to the vehicle body 22. Thus the leading edge wheel assemblies 50 turn in conjunction with each other and the trailing edge wheel assemblies 50 turn in conjunction with each other. Finally, it is noted that, when the worm rear 94 is stationary, the wheel assemblies 50 are substantially prevented from rotating relative to the vehicle body 22. That is, any force applied to the wheel assemblies by the wheel drive assemblies 52 does not cause any substantial rotation of the wheel assemblies 50 relative to the vehicle body 22.

As shown in FIG. 3, the motion assembly 26 further includes a position control assembly 100 (shown schematically). The position control assembly 100 is structured to track and control the movement of the inspection vehicle 20. Generally, the position control assembly 1100 includes an integrated circuit/computer control that executes a number of routines and which receives data from a plurality of orientation/motion sensors. The routines control the wheel drive assemblies 52 and the turning assemblies 54. Thus, by receiving data indicating orientation/motion and controlling the motion of the vehicle body 22, as well as measuring the distance to the hubs 15, 18 as discussed below, the position of the inspection vehicle 20 relative to a disk 12 may be determined and tracked.

The position control assembly 100 includes a control unit 102, a plurality of encoder assemblies 104, a gravity sensing unit 106 (all shown schematically), and at least one positioning ultrasonic transducer 108. The control unit 102 has at least one programmable logic circuit 110, a memory device 112 and at least one routine 114 (all shown schematically). The at least one positioning ultrasonic transducer 108, preferably, includes two positioning ultrasonic transducers 108A, 108B. The two positioning ultrasonic transducers 108A, 108B are structured to project an orientation signal toward the disk inner hub 15. Data representing the positioning ultrasonic transducers signal 108A, 108B is communicated to the control unit 102. That is, the at least one positioning ultrasonic transducer 108 is structured to provide data to the control unit 102. The control unit 102, and more specifically, at least one routine 114 that is executed on the at least one programmable logic circuit 110, is structured to interpret the positioning ultrasonic transducers 108 signal to determine a distance between the inspection vehicle 20 and the inner hub 15.

Further, the plurality of encoder assemblies 104 each have an encoder wheel 120 and a reader 122. Each encoder wheel 120 has a plurality of indicia 121 thereon whereby rotation of the encoder wheel 120 may be measured. That is, each reader 122 is structured to detect the encoder wheel indicia 121 as it passes past the reader 122 and to produce a signal pulse for each encoder wheel indicia 121 that is detected by the reader 122. Each reader 122 is in electronic communication with the control unit. 102. Each wheel motor assembly output shaft 90 and turning motor output shaft 92 has an associated encoder assembly 104, i.e. an encoder wheel 120 is fixed to the output shaft 90, structured to determine the rotational displacement of the output shaft 90. As the characteristics of the motion assembly 26 components, such as, but not limited to, the diameter of the shafts, wheels and gears and the gear ratios, are known, the position of the inspection vehicle 20 relative to a known starting point may be determined.

The gravity sensing unit 106 is structure to detect orientation relative to vertical and to produce a signal having data indicative of the orientation. The gravity sensing unit 106 is also in electronic communication with the control unit 102.

Thus, the control unit 102 is structured to receive data from the at least one positioning ultrasonic transducer 108, the gravity sensing unit 916 signal and signal pulses from each reader 122. The at least one routine 114 is stored on the memory device 112 and is structured to be operable on the programmable logic circuit 110. The at least one routine 114 is structured to accept the data from the at least one positioning ultrasonic transducer 108, the gravity sensing unit 106 signal, as well as the signal pulses from each reader 122. Based on this data, the position of the vehicle body 22 relative to the turbine disk 12 may be tracked. Further, the at least one routine 114 preferably includes a second routine structured to control each turning motor 91 and each wheel motor assembly 77. Accordingly, the control unit 102 is structured to track the position of the vehicle body 22 relative to the turbine disk 12 and to drive the vehicle body 22. Thus, the inspection vehicle 20 may be made to be substantially autonomous with respect to positioning. That is, the control unit 102 may move the inspection vehicle 20 to any point on the planar surface 16, and, by ensuring that the inspection vehicle 20 does not inspect an area that has been inspected before, the hubs 15 and 18 may be inspected. That is, the at least one routine 114 may contain data representing a map of the planar surface 16 and, by comparing tracking data to the map of the planar surface 16, the inspection vehicle 20 may be guided so that it does not inspect an area that has been inspected before.

It is noted that there are preferably two positioning ultrasonic transducers 108 with one positioning ultrasonic transducer 108 disposed at the leading edge 27 and one positioning ultrasonic transducer 108 disposed at the trailing edge 29. These positioning ultrasonic transducers 108A. 108B preferably operate in tandem with one positioning ultrasonic transducer 108 indicating the leading edge 27 distance relative to the inner diameter of the inner hub 15 and the other positioning ultrasonic transducer 108 indicating the trailing edge 29 distance relative to the inner diameter of the inner hub 15, thereby providing equal radial position of the lead edge 27 and trailing edge 29 of inspection vehicle 20 relative to the inner diameter on the inner hub 15. Further, and as the hub 15 is disposed generally laterally and "below" the inspection vehicle 20, the two positioning ultrasonic transducers 108A, 108B are structured to operate at an angle of between about 0 degrees and 30 degrees to the plane of the planar surface 16 and more preferably about 15 degrees to the plane of the planar surface 16. It is noted that as the position control assembly 100 collects and tracks positional data, and as the position control assembly 100 can control the drive motors, there is no need for motion control data (as used herein: data related to speed and direction) to be provided to the control unit 102 from an external source. Thus, there is also no need for communication cables structured to provide data to an external control unit. The elimination of the need for these cables also eliminates the weight associated therewith, which in turn reduces the weight of the inspection vehicle 20. When the weight of the inspection vehicle 20 is reduced, the inspection vehicle 20 may be supported by fewer and/or weaker magnets 32 in the magnetic coupling assembly 24.

Figure 9:
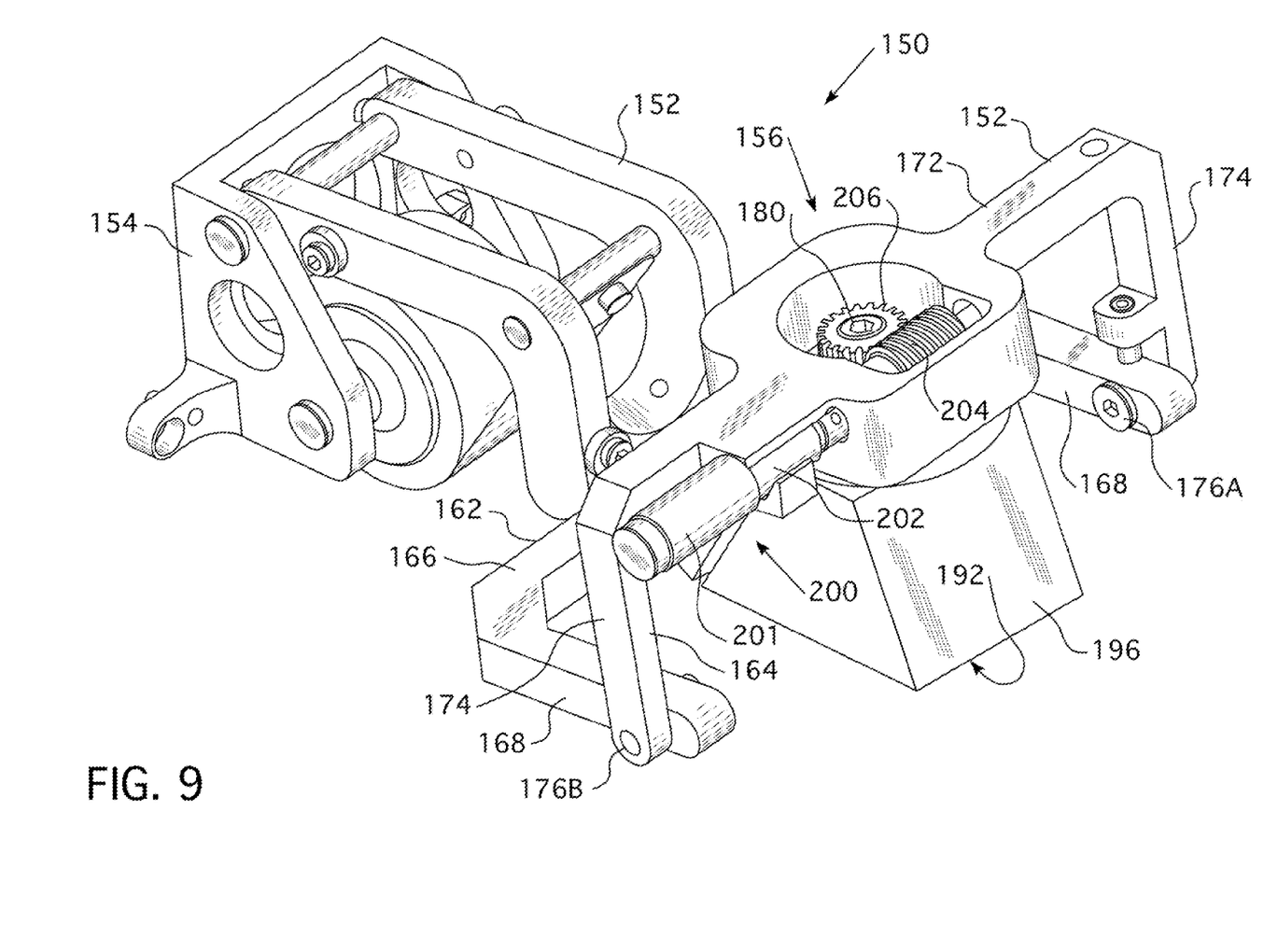
FIG. 9 is a detail isometric view of the inspection assembly.

The inspection assembly 28 is a structure used to support testing equipment and, more preferably, an ultrasonic transducer 190. Accordingly, the inspection assembly 28 includes a gimble frame assembly 150 extending from vehicle body 22 and an inspection ultrasonic transducer 190, as shown in FIG. 5 and in detail. In Figure. The gimble frame assembly 150 has a plurality of rigid members 152 wherein the rigid members 152 are rotatably coupled to each other so as to provide three axes of rotation. As shown, the gimble frame assembly 150 includes a mounting portion 154 and a gimble portion 156. The mounting portion 154 includes a rotatable coupling 158 structured to couple the gimble frame assembly 150 to the vehicle body 22. As the mounting portion 154 helps to space the inspection ultrasonic transducer 190 from the vehicle body 22 the mounting, portion 154 is typically coupled to the edge of the vehicle body 22. Preferably, the axis of rotation for the rotatable coupling 158 extends generally parallel to the edge of the vehicle body 22 to which it is coupled. Further, the rotatable coupling 158 may include a biasing device, typically a spring 160, structured to bias the gimble portion 156 to the planar surface 16. As shown in FIG. 5, a mounting portion 154 is disposed on a lateral side of the vehicle body 22. A mounting portion 154 having a greater elongation may also be coupled to the either the leading or trailing edges 27, 29 of the vehicle body 22, as shown in FIG. 2.

The gimble portion 156 preferably includes two U-shaped yokes, that is, a first and second yoke 162, 164. The first yoke 162 has an elongated cross member 166 and two tines 168 the tines 168 extending perpendicular to, and from the tips of, the cross member 166. The first yoke tines 168 extend in the same direction and generally within the same plane. Although structured to rotate, the plane of the first yoke 162 is generally parallel to the planar surface 16. A first pivot rod 170 is disposed at a medial location on the cross member 166 and also extends in a plane generally parallel to the planar surface 16. The first pivot rod 170 is further coupled to the mounting portion 154. The first pivot rod 170 provides one axis of rotation for the gimble frame assembly 150.

The second yoke 164 has an elongated cross member 172 and two tines 174, the tines 174 extending perpendicular to, and from the tips of, the cross member 172. The second yoke tines 174 extend in the same direction and generally within the same plane. Two second pivot rods 176A, 1768 couple the first and second yokes 162, 164 together. More specifically, the first and second yokes 162, 164 are rotatably coupled at the distal ends of the first yoke tines 168 and the second yoke tines 174. The axis of rotation for the second pivot rods 176A, 176B are aligned. The axis of rotation for the second pivot rods 176A, 1768 extends generally perpendicular to the axis of rotation for the first pivot rod 170 and generally parallel to the planar surface 16. The second pivot rods 176A, 176B provide a second axis of rotation for the gimble frame assembly 150.

An axle 180 is disposed at the medial portion of the second yoke 164 and extends generally perpendicular to the planar surface 16. The lower end of the axle 180 is coupled to the inspection ultrasonic transducer 190. The axle 180 provides the third axis of rotation for the gimble frame assembly 150. A gimble drive assembly 200 includes a motor 201 having an extended output shaft 202 with a worm gear 204 disposed thereon. The gimble drive assembly motor output shaft 202 extends generally parallel to the second yoke cross member 172. The assemble drive assembly worm gear 204 is disposed adjacent to the axle 180. The axle 180 may have a gear 206 fixed thereto that is structured to operatively engage the nimble motor worm gear 204. The ginible drive assembly motor 201 is structured to be controlled by, and is in electronic communication with, the control unit 102. Actuation of the gimble drive assembly motor 201 causes the axle 180, and therefore the inspection ultrasonic transducer 190 to rotate on the center of the inspection transducer.

The inspection ultrasonic transducer 190 is fixed, directly or indirectly, to the axle 180. The inspection ultrasonic transducer 190 has a generally planar inspection face 192 that extends generally parallel to the planar surface 16. It is noted that the rotatable coupling spring 160, which is disposed at the interface between the vehicle body 22 and the gimble frame assembly 150, biases the inspection ultrasonic transducer inspection face 192 toward the planar surface 16, that is, toward the surface of the turbine disk. 12.

While specific embodiments of the invention have been described in detail, it will be appreciated by those skilled in the an that various modifications and alternatives to those details could be developed in light of the overall teachings of the disclosure. Accordingly, the particular embodiments disclosed are meant to be illustrative only and not limiting as to the scope of the invention which is to be given the breath of the appended claims and any and all equivalents thereof

What is claimed is:

1. An inspection vehicle structured to inspect a turbine disk while said turbine disk is in situ, said inspection vehicle comprising:
    a body structured to support a plurality of components;
    a magnetic coupling assembly coupled to said body and structured to movably couple said body to said turbine disk;
    a motion assembly structured to move said body over said turbine disk; and
    an inspection assembly structured to inspect said turbine disk.

2. The inspection vehicle of claim 1 wherein:
    said motion assembly includes a plurality of wheel assemblies, a plurality of wheel drive assemblies, and a plurality of turning assemblies;
    each said wheel assembly rotatably coupled to said body and having a housing assembly and a wheel;
    each turning assembly structured to rotate a wheel assembly relative to said body; and
    each said drive assembly structured to rotate the associated wheel.

3. The inspection vehicle of claim 2 wherein:
each said wheel assembly wheel includes an outer surface; and
each said wheel outer diameter surface having a rigid portion extending about the circumference of said outer surface and a pliable portion extending about the circumference of said outer surface.

4. The inspection vehicle of claim 3 wherein:
said body has a wheel side;
said magnetic coupling assembly includes a plurality of magnets coupled to said body wheel side; and
wherein when said body is coupled to said turbine disk, each said magnet is operatively spaced from said turbine disk.

5. The inspection vehicle of claim 4 wherein at least one magnet in said plurality of magnets is coupled to said body by an adjustable coupling device whereby the spacing between said turbine disk and said at least one magnet coupled to said body by an adjustable coupling device may be altered.

6. The inspection vehicle of claim 3 wherein:
each said wheel assembly wheel has a body;
each said wheel assembly wheel body and outer surface rigid portion being steel; and
each said wheel assembly wheel outer surface pliable portion being rubber.

7. The inspection vehicle of claim 2 wherein:
each said wheel drive assembly includes a motor having an output shaft and a bevel gear assembly;
each said wheel drive assembly bevel gear assembly operatively engaging said wheel drive assembly motor output shaft and an associated said wheel;
whereby each said wheel rotates upon the actuation of the associated wheel drive assembly motor; and
whereby each wheel acts as a drive wheel.

8. The inspection vehicle of claim 2 wherein:
said inspection assembly includes a gimble frame assembly extending from said body and an inspection ultrasonic transducer;
said gimble frame assembly having a plurality of rigid members, said rigid members rotatably coupled to each other whereby said gimble frame assembly provides three axes of rotation;
said gimble frame assembly structured to support an inspection ultrasonic transducer; and
said inspection ultrasonic transducer coupled to said gimble frame assembly.

9. The inspection vehicle of claim 8 wherein:
said inspection ultrasonic transducer has an inspection face structured to extend generally parallel to the surface of said turbine disk;
said gimble frame assembly includes drive assembly structured to rotate said inspection ultrasonic transducer about an axis extending generally normal to said inspection ultrasonic transducer inspection face.

10. The inspection vehicle of claim 9 wherein:
said gimble assembly includes an axle extending generally perpendicular to the plane of said turbine disk, said axle having a gear thereon;
said gimble frame assembly drive assembly includes a motor, an output shaft and a worm gear;
said gimble drive assembly motor shaft extending generally parallel to the plane of said turbine disk;
said gimble drive assembly worm gear disposed on said gimble drive assembly output shaft;
said gimble drive assembly worm gear operatively engaging said axle gear; and
said inspection ultrasonic transducer fixed to said axle.

11. The inspection vehicle of claim 8 wherein said gimble frame assembly includes a spring structured to bias said inspection ultrasonic transducer inspection face towards the surface of said turbine disk.

12. An inspection vehicle structured to inspect a turbine disk while said turbine disk is in situ, said inspection vehicle comprising:
a movable body structured to support a plurality of components;
a magnetic coupling assembly coupled to said body and structured to movably couple said body to said turbine disk;
a motion assembly structured to move said body over said turbine disk; and
an inspection assembly structured to inspect said turbine disk.

13. The inspection vehicle of claim 12 wherein:
said motion assembly includes a plurality of wheel assemblies and a plurality of turning assemblies;
each said wheel assembly rotatably coupled to said body; and
each turning assembly structured to rotate a wheel assembly relative to said body.

14. The inspection vehicle of claim 12 wherein:
said motion assembly includes a plurality of wheel drive assemblies;
each said wheel assembly having a housing assembly and a wheel; and
each said drive assembly structured to rotate the associated wheel.

15. The inspection vehicle of claim 14 wherein:
said body has a wheel side;
said magnetic coupling assembly includes a plurality of magnets coupled to said body wheel side; and
wherein when said body is coupled to said turbine disk, each said magnet is operatively spaced from said turbine disk.

16. The inspection vehicle of claim 15 wherein at least one magnet in said plurality of magnets is coupled to said body by an adjustable coupling device whereby the spacing between said turbine disk and said at least one magnet coupled to said body by an adjustable coupling device may be altered.

17. An inspection vehicle structured to inspect a turbine disk while said turbine disk is in situ, said inspection vehicle comprising:
a body structured to support a plurality of components;
a magnetic coupling assembly coupled to said body and structured to movably couple said body to said turbine disk;
a motion assembly structured to move said body over said turbine disk;
said motion assembly includes a plurality of wheel assemblies and a plurality of turning assemblies;
each said wheel assembly rotatably coupled to said body;
each turning assembly structured to rotate a wheel assembly relative to said body; and
an inspection assembly structured to inspect said turbine disk.

18. The inspection vehicle of claim 17 wherein:
said body has a wheel side;
said magnetic coupling assembly includes a plurality of magnets coupled to said body wheel side; and
wherein when said body is coupled to said turbine disk, each said magnet is operatively spaced from said turbine disk.

19. The inspection vehicle of claim 18 wherein at least one magnet in said plurality of magnets is coupled to said body by an adjustable coupling device whereby the spacing between said turbine disk and said at least one magnet coupled to said body by an adjustable coupling device may be altered.

20. The inspection vehicle of claim 17 wherein:
- said inspection assembly includes a gimble frame assembly extending from said body and an inspection ultrasonic transducer;
- said gimble frame assembly having a plurality of rigid members, said rigid members rotatably coupled to each other whereby said gimble frame assembly provides three axes of rotation;
- said gimble frame assembly structured to support an inspection ultrasonic transducer; and
- said inspection ultrasonic transducer coupled to said gimble frame assembly.

* * * * *